United States Patent
Igarashi et al.

(10) Patent No.: US 7,955,676 B2
(45) Date of Patent: Jun. 7, 2011

(54) MEDICAL TUBES

(75) Inventors: Kouichi Igarashi, Ichihara (JP);
Sadamu Shirokuma, Kimitsu (JP);
Ryoji Mori, Ichihara (JP); Isamu Tateishi, Naruto (JP); Hitoshi Mori, Tokushima (JP); Rie Ishii, Amagasaki (JP)

(73) Assignees: Mitsui Chemicals, Inc., Tokyo (JP);
Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 11/791,526

(22) PCT Filed: Nov. 25, 2005

(86) PCT No.: PCT/JP2005/021739
§ 371 (c)(1),
(2), (4) Date: May 24, 2007

(87) PCT Pub. No.: WO2006/057370
PCT Pub. Date: Jun. 1, 2006

(65) Prior Publication Data
US 2008/0215016 A1    Sep. 4, 2008

(30) Foreign Application Priority Data

Nov. 26, 2004  (JP) .................. 2004-343198

(51) Int. Cl.
*C08L 23/10* (2006.01)
*C08L 23/02* (2006.01)
(52) U.S. Cl. ............. 428/36.92; 428/34.1; 525/240; 525/191; 526/351
(58) Field of Classification Search ............ 428/36.9, 428/36.92; 525/95, 240
See application file for complete search history.

(56) References Cited

U.S. PATENT DOCUMENTS
6,977,105 B1  12/2005  Fujieda et al.
(Continued)

FOREIGN PATENT DOCUMENTS
EP  0 814 127 A1  12/1997
(Continued)

OTHER PUBLICATIONS

Chinese Office Action mailed Jun. 5, 2009, received in corresponding China Application No. 2005800405295.
(Continued)

*Primary Examiner* — Rena L Dye
*Assistant Examiner* — Ellen S Wood
(74) *Attorney, Agent, or Firm* — Foley & Lardner LLP

(57) ABSTRACT

Medical tubes are well balanced in transparency, flexibility, heat resistance, scratch resistance and rubber elasticity.
The medical tubes including a propylene polymer composition (A) that contains a polymer with propylene units, at least part of the polymer having an isotactic structure and the total of the propylene units of the polymer being in an amount of 65 to 82 mol % (the total of the structural units of the polymer in the composition is 100 mol %), and that satisfies the following (a1), (a2) and (b1):
 (a1) the modulus in tension is in the range of 5 to 25 MPa as determined in accordance with JIS K 6301;
 (a2) the penetration temperature is 120° C. or above as determined in accordance with JIS K 7196; and
 (b1) when a tube being made of the composition (A) and having an inner diameter of 2.1 mm, an outer diameter of 3.5 mm and a length of 20 cm is looped by inserting both ends thereof into a hollow jig having a hole 10 mm in diameter and 5 mm in height and, then, the both ends of the tube are pulled down until a kink occurs in the loop, the distance H from the upper surface of the jig to the upper end of the loop is not more than 60 mm.

9 Claims, 1 Drawing Sheet

U.S. PATENT DOCUMENTS

| | | |
|---|---|---|
| 2001/0021430 A1 | 9/2001 | Shimada |
| 2003/0130430 A1* | 7/2003 | Cozewith et al. .............. 525/240 |
| 2005/0131160 A1* | 6/2005 | Shimizu et al. ................ 525/242 |
| 2006/0057321 A1* | 3/2006 | Mori et al. .................. 428/36.92 |
| 2006/0247381 A1 | 11/2006 | Mori et al. |

FOREIGN PATENT DOCUMENTS

| | | |
|---|---|---|
| EP | 0980892 A1 | 2/2000 |
| EP | 1 106 647 A2 | 6/2001 |
| EP | 1 374 941 A1 | 1/2004 |
| EP | 1 471 085 A1 | 10/2004 |
| JP | 05-084293 | 4/1993 |
| JP | 6-136200 | 5/1994 |
| JP | 7-268145 | 10/1995 |
| JP | 8-283491 | 10/1996 |
| JP | 11-255835 | 9/1999 |
| JP | 2000-063577 | 2/2000 |
| JP | 2000-334038 | 12/2000 |
| JP | 2001-001432 | 1/2001 |
| JP | 2001-46492 | 2/2001 |
| JP | 2001-104473 | 4/2001 |
| JP | 2001-252348 | 9/2001 |
| JP | 2002-143292 | 5/2002 |
| JP | 2003-699 | 1/2003 |
| JP | 2003-292700 | 10/2003 |
| WO | WO 2004-067627 | 8/2004 |
| WO | WO 2004/106430 A1 | 12/2004 |

OTHER PUBLICATIONS

European Search Report mailed May 25, 2010 in corresponding Application No. EP 05809722.1.

* cited by examiner

MEDICAL TUBES

FIELD OF THE INVENTION

The present invention relates to medical tubes, and particularly to tubes for introducing or withdrawing substances into or from a body. More specifically, the invention relates to indwelling catheters inserted and placed in a vessel for transfusion, blood sampling and hemodynamic monitoring, and also relates to injection of infusion solutions and chemicals into animal bodies, particularly human bodies. Still more specifically, the invention relates to flexible medical tubes suited for transporting medical fluids such as blood and infusion solutions, the tubes being made of a propylene polymer composition excellent in transparency, flexibility, scratch resistance, heat resistance and rubber elasticity.

BACKGROUND OF THE INVENTION

Medical tubes include tubes for introducing or withdrawing substances into or from a body, and catheters inserted into a body for examination or treatment. Specific examples of the medical tubes include catheters such as urinary catheters, stomach catheters and suction catheters; tubes such as infusion tubes, enteral feeding tubes, peritoneal dialysis tubes, blood transfusion tubes and tubes connected to urinary catheters to guide urine to urine collection bags; circuit tubes used in blood circuits for hemodialysis, artificial heart-lung machines and plasmapheresis; and tubes for transporting substances in the medical field. The transporting tubes for medical substances include tubes attached to multiple blood bags and tubes for connecting an aspirator and a catheter. Many of the conventional medical tubes are made of polyvinyl chloride that is inexpensive and possesses excellent kink resistance and a certain level of flexibility (pliancy). However, alternative materials have been required because of environmental concerns.

The alternatives studied so far include styrene elastomer compositions (JP-A-2000-63577, JP-A-2001-252348 and JP-A-2001-1432), thermoplastic polyurethane compositions (JP-A-H05-84293 and JP-A-2001-46492), and syndiotactic 1,2-polybutadiene compositions (JP-A-2000-334038 and JP-A-2001-104473). The fact, however, is that these compositions have low versatility and practical utility due to insufficient flexibility and high costs. (Patent Documents 1-7)

To achieve the versatility and practical utility, studies have been made on copolymers of ethylene and α-olefins of 3 or more carbon atoms, and acid copolymers of ethylene and vinyl acetate or the like. However, none has satisfied performances required such as flexibility, heat resistance and kink resistance.

Meanwhile, polypropylenes include isotactic polypropylenes and syndiotactic polypropylenes. Particularly, the isotactic polypropylenes are inexpensive and excellent in transparency and heat resistance, and are therefore widely used in various packaging materials and industrial materials. However, their flexibility is unsatisfactory. To solve this problem, compositions have been studied in which flexible materials such as ethylene elastomers are blended with the polypropylenes. However, none has satisfied performances required. Medical tubes of syndiotactic polypropylene resin compositions have recently been proposed (WO 2004/067627), but their heat resistance and breaking strength have been insufficient. (Patent Document 8)

[Patent Document 1] JP-A-2000-63577
[Patent Document 2] JP-A-2001-252348
[Patent Document 3] JP-A-2001-1432
[Patent Document 4] JP-A-H05-84293
[Patent Document 5] JP-A-2001-46492
[Patent Document 6] JP-A-2000-334038
[Patent Document 7] JP-A-2001-104473
[Patent Document 8] WO 2004/067627

DISCLOSURE OF THE INVENTION

The present invention aims to solve the aforementioned problems in the background art. It is therefore an object of the invention to provide medical tubes made of a propylene polymer composition that are well balanced and excellent in transparency, flexibility, heat resistance, scratch resistance and rubber elasticity.

The present inventors have made intensive studies of medical tubes capable of solving the conventional problems and having high heat resistance, flexibility and kink resistance, and they have arrived at medical tubes with excellent balance of properties that are obtained by use of a specific propylene polymer composition. Specifically, the medical tubes according to the invention:

comprise a propylene polymer composition (A) that comprises a polymer with propylene units, at least part of the polymer having an isotactic structure and the total of the propylene units of the polymer being in an amount of 65 to 82 mol % (the total of the structural units of the polymer in the composition is 100 mol %), and that satisfies the following (a1), (a2) and (b1):

(a1) the modulus in tension is in the range of 5 to 25 MPa as determined in accordance with JIS K 6301;

(a2) the penetration temperature is 120° C. or above as determined in accordance with JIS K 7196; and (b1) when a tube being made of the composition (A) and having an inner diameter of 2.1 mm, an outer diameter of 3.5 mm and a length of 20 cm is looped by inserting both ends thereof into a hollow jig having a hole 10 mm in diameter and 5 mm in height and, then, the both ends of the tube are pulled down until a kink occurs in the loop, the distance H from the upper surface of the jig to the upper end of the loop is not more than 60 mm.

The medical tubes made of the specific propylene polymer composition are well balanced in transparency, flexibility, heat resistance, scratch resistance and rubber elasticity, and show superior kink resistance that has been a problem in the art.

PREFERRED EMBODIMENTS OF THE INVENTION

Figure 1:
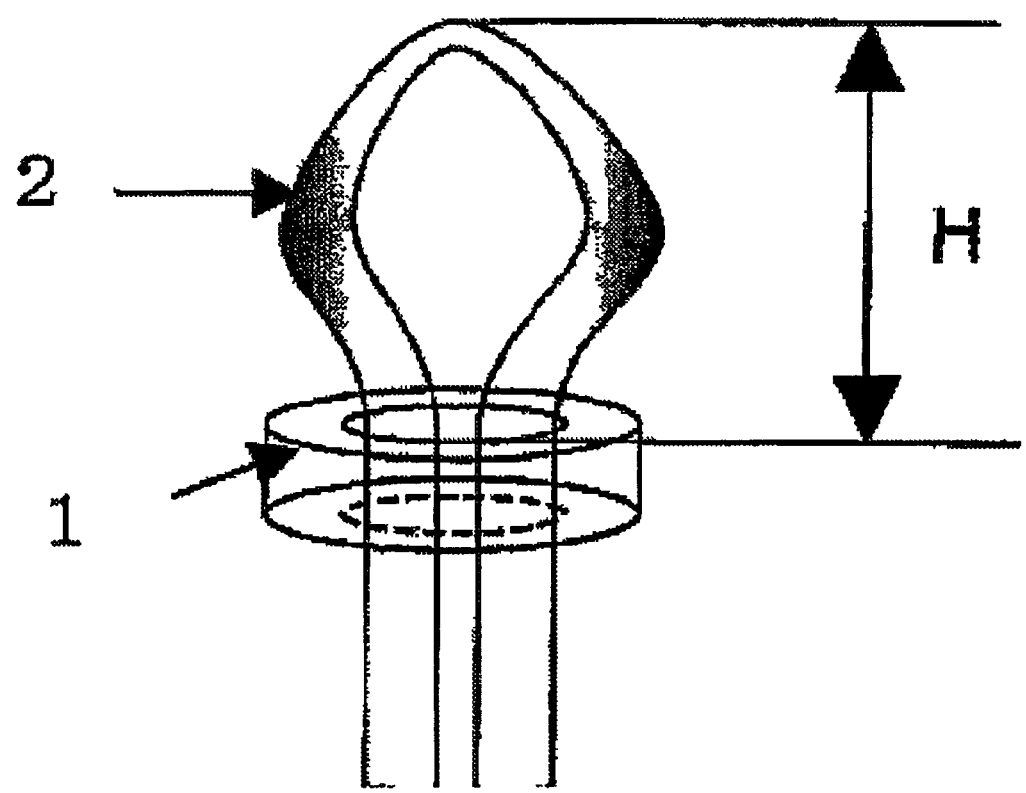
FIG. 1 illustrates an evaluation method for kink resistance.
1 . . . Hollow cylinder (jig)
2 . . . Tube

The medical tubes made of the specific propylene polymer composition according to the present invention will be described in detail hereinbelow.

Propylene Polymer Composition (A)

The propylene polymer composition (A) for use in the invention contains a polymer having propylene units (hereinafter, also referred to the "propylene polymer"), at least part of the propylene polymer having an isotactic structure. The propylene polymer composition (A) contains the propylene units in an amount of 65 to 82 mol %, preferably 69 to 80 mol %, more preferably 72 to 79 mol % to the total (100 mol %) of the structural units of the propylene polymer in the composition (A). The propylene polymer composition (A) has (a1) a modulus in tension in the range of 5 to 25 MPa as determined in accordance with JIS K 6301 and (a2) a penetration temperature of 120° C. or above as determined in accordance with JIS K 7196.

The propylene polymer contained in the propylene polymer composition (A) is characterized in that at least part thereof has an isotactic structure.

As used herein, the propylene polymer having an isotactic structure means a polymer in which triad tacticity of the head-to-tail coupled propylene unit sequences as determined by $^{13}$C-NMR is at least 95.0%, preferably at least 96.0%, more preferably at least 97.0%, the triad tacticity being the ratio of triad sequences of head-to-tail coupled propylene units with the methyl groups branching in the same direction, to arbitrary triad sequences of propylene units in the polymer chains. The procedures for determination of the triad tacticity of head-to-tail coupled propylene unit sequences by $^{13}$C-NMR are described in JP-A-H08-73532.

The propylene polymer in the polymer composition (A) may contain structural units other than the propylene units without limitation, as long as such structural units can make up organic polymers. Preferred are structural units constituting common polyolefins, such as ethylene units, C4-20 α-olefin units, diene units, triene units and polyene units, with the ethylene units and the C4-8 α-olefin units being particularly preferred. Preferably, the polymer contains two or more types of these structural units, and particularly preferably contains two types of structural units selected from the ethylene units and C4-8 α-olefin units. For example, the propylene units as used herein are structural units derived from propylene monomers, which applies also to other structural units.

A particularly preferred-embodiment of the propylene polymer composition (A) is described below. Particularly preferably, the propylene polymer composition (A) contains, based on 100 parts by weight thereof: 1 to 40 parts by weight of polypropylene having an isotactic structure (hereinafter, also referred to as the "isotactic polypropylene (i)); and 60 to 99 parts by weight of a propylene/ethylene/α-olefin random copolymer having an isotactic structure and containing 45 to 89 mol % of propylene units, 10 to 25 mol % of ethylene units and optionally 0 to 30 mol % of C4-20α-olefin units (hereinafter, also referred to as the "propylene/ethylene/α-olefin random copolymer (ii)) (wherein at least one of the contents of the ethylene units and the C4-20 α-olefin units is not 0 mol %).

Isotactic Polypropylene (i)

The isotactic polypropylene (i) used in the invention is a specific propylene polymer having the following properties. As long as the properties described below are satisfied, the propylene polymer may be a homopolypropylene, a propylene/α-olefin random copolymer or a propylene block copolymer. Preferably, the polymer is a homopolypropylene or a propylene/α-olefin random copolymer.

The isotactic polypropylene (i) ranges in melt flow rate (MFR; ASTM D1238, 230° C., 2.16 kg load) from 0.01 to 400 g/10 min, preferably from 0.1 to 90 g/10 min. The DSC melting point thereof is 120° C. or above, preferably 130° C. or above, more preferably 150° C. or above.

MFR of the isotactic polypropylene exceeding 400 g/10 min may lead to poor impact resistance (Izod impact strength) of the composition.

When the isotactic polypropylene (i) is a propylene/α-olefin random copolymer, the α-olefin is preferably selected from ethylene and α-olefins of 4 to 20 carbon atoms. The propylene/α-olefin random copolymer desirably contains the α-olefin units in an amount of 0.3 to 7 mol %, preferably 0.3 to 6 mol %, more preferably 0.3 to 5 mol % based on 100 mol % of the total of the structural units in the copolymer.

The isotactic polypropylene (i) may be produced by various processes, for example using a stereoregular catalyst. More specifically, it can be synthesized in the presence of a catalyst composed of a solid titanium catalyst component, an organometallic compound catalyst component and optionally an electron donor. Specific examples of the solid titanium catalyst components include solid titanium catalyst components composed of titanium trichloride or a titanium trichloride composition on a carrier having a specific surface area of 100 m$^2$/g or more; and solid titanium catalyst components in which magnesium, a halogen, an electron donor (preferably an aromatic carboxylic acid ester or an alkyl-containing ether) and titanium as essential components are supported on a carrier having a specific surface area of 100 m$^2$/g or more. Metallocene catalysts are also useful.

Preferred examples of the organometallic compound catalyst components include organoaluminum compounds such as trialkylaluminums, dialkylaluminumhalides, alkylaluminumsesquihalides and alkylaluminumdihalides. The organoaluminum compounds may be selected appropriately depending on the type of the titanium catalyst component used.

Examples of the electron donors include organic compounds containing a nitrogen atom, a phosphorus atom, a sulfur atom, a silicon atom or a boron atom. Ester compounds and ether compounds containing these atoms are preferable.

The catalyst may be activated by a method such as co-grinding, and the above-mentioned olefins may be prepolymerized.

Propylene/Ethylene/α-Olefin Random Copolymer (ii)

The propylene/ethylene/α-olefin random copolymer (ii) possesses an isotactic structure and contains propylene units in an amount of 45 to 89 mol %, preferably 45 to 80 mol %, more preferably 50 to 75 mol %, ethylene units in an amount of 10 to 25 mol %, preferably 10 to 23 mol %, more preferably 12 to 23 mol %, and optionally C4-20 α-olefin units (a) in an amount of 0 to 30 mol %, preferably 0 to 25 mol %, more preferably 0 to 20 mol %.

Containing the propylene units, ethylene units and optional C4-20 α-olefin units in the above amounts, the propylene/ethylene/α-olefin random copolymer (ii) tends to show good compatibility with the isotactic polypropylene (i); further, the propylene polymer composition obtained will exhibit sufficient transparency, flexibility, heat resistance and scratch resistance.

In terms of tackiness of tubes, it is particularly preferable that the propylene/ethylene/α-olefin random copolymer (ii) contains the propylene units in an amount of 65 to 71 mol %, preferably 67 to 69 mol %, the ethylene units in an amount of 12 to 15 mol %, preferably 13 to 14 mol %, and the C4-20 α-olefin units (a) in an amount of 17 to 23 mol %, preferably 18 to 21 mol %.

The tackiness of tubes is important especially when the tube is used in such a manner that it is pinched by application of force to interrupt temporarily the flow of fluid in the tube, and thereafter the force is released to restart the fluid flow. Such tubes include infusion tubes and blood transfusion tubes. Low tube tackiness is preferable in these applications because the fluid restarts to flow as soon as the tube is released from the force.

That is, the medical tubes of the invention are particularly suitable for use in a set including a tube and means for deforming the tube to interrupt the fluid flow and/or means for deforming the tube to control the fluid flow. Examples of the means for deforming the tube to interrupt the fluid flow and/or the means for deforming the tube to control the fluid flow include clamps. Particularly preferably, the medical tubes of the invention are medical tubes that constitute part of medical devices such as infusion circuits (infusion sets) and blood transfusion circuits (blood transfusion sets).

The intrinsic viscosity [η] at 135° C. in decalin of the propylene/ethylene/α-olefin random copolymer (ii) is desirably in the range of 0.01 to 10 dl/g, preferably 0.05 to 10 dl/g. The propylene/ethylene/α-olefin random copolymer (ii) having this intrinsic viscosity [η] will show superior characteristics such as weather resistance, ozone resistance, thermal aging resistance, low temperature properties and dynamic fatigue resistance.

The propylene/ethylene/α-olefin random copolymer (ii) has a stress at 100% strain (M100) of not more than 4 MPa, preferably not more than 3 MPa, more preferably not more than 2 MPa when determined with respect to a JIS No. 3 dumbbell specimen, with a span of 30 mm at a stress rate of 30 mm/min and at 23° C. in accordance with JIS K 6301. The propylene/ethylene/α-olefin random copolymer (ii) satisfying this condition shows excellent flexibility, transparency and rubber elasticity.

The propylene/ethylene/α-olefin random copolymer (ii) has crystallinity of not more than 20%, preferably from 0 to 15% as measured by X-ray diffractometry. Further, the propylene/ethylene/α-olefin random copolymer (ii) desirably has a single glass transition temperature, and the glass transition temperature Tg as measured with a differential scanning calorimeter (DSC) is desirably −10° C. or less, preferably −15° C. or less. The propylene/ethylene/α-olefin random copolymer (ii) having this glass transition temperature Tg shows excellent cold resistance and low temperature properties.

When the propylene/ethylene/α-olefin random copolymer (ii) has a melting point (Tm, ° C.) in a DSC (differential scanning calorimeter) endothermic curve, the heat of fusion ΔH is 30 J/g or less, and the propylene unit content (hereinafter, also referred to as the "C3 content") (mol %) and the heat of fusion ΔH (J/g) satisfy the following relation:

$$\Delta H < 345 \, \text{Ln}(C3 \, \text{content}(\text{mol}\%)) - 1492$$

(with the proviso that 76≦C3 content (mol %)≦90)

The GPC molecular weight distribution (Mw/Mn, in terms of polystyrene, Mw: weight-average molecular weight, Mn: number-average molecular weight) is desirably 4.0 or less, preferably 3.0 or less, more preferably 2.5 or less.

The propylene/ethylene/α-olefin random copolymer (ii) may be partially modified by grafting a polar monomer. Examples of the polar monomers include hydroxyl group-containing ethylenically unsaturated compounds, amino group-containing ethylenically unsaturated compounds, epoxy group-containing ethylenically unsaturated compounds, aromatic vinyl compounds, unsaturated carboxylic acids and derivatives thereof, vinyl ester compounds and vinyl chloride.

The modified propylene/ethylene/α-olefin copolymer may be obtained by graft; polymerization of the polar monomer to the propylene/ethylene/α-olefin random copolymer (ii). The graft polymerization of the polar monomer to the propylene/ethylene/α-olefin copolymer (ii) generally involves the polar monomer in an amount of 1 to 100 parts by weight, preferably 5 to 80 parts by weight per 100 parts by weight of the propylene/ethylene/α-olefin random copolymer (ii). The graft polymerization is generally performed in the presence of a free-radical initiator.

Examples of the free-radical initiators include organic peroxides and azo compounds.

The free-radical initiator may be used directly by being mixed with the propylene/ethylene/α-olefin random copolymer (ii) and the polar monomer, or may be used after dissolved in a small amount of an organic solvent. The organic solvents used herein are not particularly limited as long as they can dissolve the free-radical initiator.

A reducing substance may be used in the graft polymerization of the polar monomer to the propylene/ethylene/α-olefin random copolymer (ii). The use of the reducing substance increases the amount of the polar monomer grafted.

The graft modification of the propylene/ethylene/α-olefin random copolymer (ii), with the polar monomer may be carried out in a conventional manner. For example, the propylene/ethylene/α-olefin copolymer (ii) may be dissolved in an organic solvent, and the polar monomer and the free-radical initiator may be added to the solution to perform reaction at 70 to 200° C., preferably 80 to 190° C., for 0.5 to 15 hours, preferably 1 to 10 hours.

Alternatively, the modified propylene/ethylene/α-olefin copolymer may be produced by reacting the propylene/ethylene/α-olefin random copolymer (ii) and the polar monomer in the absence of a solvent with use of an extruder or the like. This reaction is desirably conducted at a temperature not less than the melting point of the propylene/ethylene/α-olefin random copolymer (ii), specifically at 120 to 250° C., for 0.5 to 10 minutes.

The modified propylene/ethylene/α-olefin copolymer obtained as described above desirably has a modification amount (amount of polar monomer grafted) in the range of 0.1 to 50 wt %, preferably 0.2 to 30 wt %, more preferably 0.2 to 10 wt %.

When the propylene polymer composition (A) contains the modified propylene/ethylene/α-olefin copolymer, it shows superior adhesion and compatibility with other resins and can give formed products having improved-surface wettability.

Production of Propylene/Ethylene/α-Olefin Random Copolymer (ii)

The propylene/ethylene/α-olefin random copolymer (ii) may be produced using a metallocene catalyst as used for synthesizing the isotactic polypropylene (i), but the production is not limited thereto.

Production of Propylene Polymer Composition (A)

To produce the propylene polymer composition (A), the aforementioned components may be mixed in the specified amounts by a number of known processes, for example by multistage polymerization or mixing with a Henschel mixer, a V-type blender, a ribbon blender or a Tumbler mixer, or by mixing as above and melt-kneading the mixture with a single screw extruder, a twin screw extruder, a kneader or a Banbury mixer, followed by granulating or pulverizing.

The propylene polymer composition (A) may contain additives as required while still achieving the objects of the invention. Examples of the additives include weathering stabilizers, heat stabilizers, antistatic agents, anti-slip agents, anti-blocking agents, anti-fogging agents, lubricants, pigments, dyes, plasticizers, anti-aging agents, hydrochloric acid absorbents and antioxidants. Further, "other copolymer" (elastomer or elastomer resin) as described below may be used without departing from the effects of the invention and while still achieving the objects of the invention.

The propylene polymer composition (A) as described above can give formed products well balanced and excellent in transparency, impact resistance, flexibility, heat resistance, scratch resistance and rubber elasticity.

Other Copolymer

The propylene polymer composition (A) for use in the invention may contain "other copolymer" (elastomer or elastomer resin) as required.

Examples of the "other copolymers" include ethylene/α-olefin random copolymers (iii), ethylene/diene copolymers (iv) and ethylene/triene copolymers (v). These copolymers may be used singly or in combination of two or more kinds.

The "other copolymer" may be used in an amount of 0 to 30 parts by weight, preferably 0 to 20 parts by weight per 100 parts by weight of the isotactic polypropylene (i). When the composition contains the "other copolymer" in the above amount, it can give formed products well balanced in flexibility, transparency and low temperature impact resistance.

Additional Description of Propylene Polymer Composition (A)

The propylene polymer composition (A) used in the invention is free of styrene or ethylene block copolymers. Further, the propylene polymer composition (A) preferably meets any of (I) to (III):

(I) The composition satisfies all the following (A), (B), (C) and (D).
(II) The composition satisfies the following (E).
(III) The composition satisfies all the following (A), (B), (C), (D) and (E).

By "the propylene polymer composition (A) is free of styrene or ethylene block copolymers", it is understood that the content of styrene or ethylene block copolymers in the propylene polymer composition is not more than 10 wt %, preferably not more than 5 wt %, still preferably not more than 2 wt %.

(A) The composition shows a loss tangent (tan δ) peak at a temperature in the range of −25 to 25° C. according to dynamic viscoelasticity measurement (10 rad/s) in a torsion mode, and the peak value is 0.5 or above.

(B) The storage moduli G' (20° C.) and G' (100° C.) from the dynamic viscoelasticity measurement have a ratio (G' (20° C.)/G' (100° C.)) of not more than 5.

(C) The penetration temperature (° C.) determined in accordance with JIS K 7196 is not less than 120° C.

(D) The composition has a permanent set of not more than 20% as determined after the composition fixed between chucks 30 mm apart is 100% strained at a stress rate of 30 mm/min, maintained for 10 minutes and released for 10 minutes.

(E) The composition contains the isotactic polypropylene (i) in an amount of 1 to 40 parts by weight, preferably 1 to −30 parts by weight, more preferably 1 to 25 parts by weight, and the propylene/ethylene/α-olefin random copolymer (ii) in an amount of 60 to 99 parts by weight, preferably 70 to 99 parts by weight, more preferably 75 to 99 parts by weight (based on the weight of the propylene polymer composition (A) (100 parts by weight)).

In the property (A), the loss tangent (tan δ) at −25 to 25° C. is 0.5 or above, preferably in the range of 0.5 to 2.5, more preferably in the range of 0.6 to 2. When the loss tangent (tan δ) at −25 to 25° C. is lower than 0.5, the propylene polymer composition tends to show insufficient flexibility or, even if having flexibility, tends to be poor in scratch resistance.

In the property (B), the ratio (G' (20° C.)/G' (100° C.)) of storage moduli G' (20° C.) and G' (100° C.) is not more than 5, preferably not more than 4, still preferably not more than 3.5. When the ratio (G' (20° C.)/G' (100° C.)) of storage moduli G' (20° C.) and G' (100° C.) exceeds 5, the propylene polymer composition tends to show surface stickiness to deteriorate handling properties and tends to fail to exhibit sufficient heat resistance.

In the property (C), the penetration temperature (° C.) determined in accordance with JIS K 7196 is not less than 120° C., preferably in the range of 121 to 135° C., more preferably in the range of 125 to 135° C. When the penetration temperature is below 120° C., the propylene polymer composition cannot be used in applications requiring heat sterilization or the like.

In the property (D), the permanent set is not more than 20%, preferably not more than 18%, still preferably not more than 16% as determined after a dumbbell specimen 50 mm in length, 5 mm in width and 1 mm in thickness is fixed with gauge lines 30 mm apart, then strained at a stress rate of 30 mm/min to 100% strain, maintained for 10 minutes and released for 10 minutes. When the permanent set exceeds 20%, the rubber elasticity tends to be low, and the composition cannot be used in applications requiring stretching and restoring properties.

The propylene polymer composition (A) has a modulus in tension (Young's modulus) of 5 to 25 MPa, preferably 5 to 23 MPa, more preferably 7 to 20 MPa as determined in accordance with JIS 6301.

The propylene polymer composition (A) generally has a melt flow rate (ASTM D1238, 230° C., 2.16 kg load) of 0.0001 to 1000 g/10 min, preferably 0.0001 to 900 g/10 min, more preferably 0.0001 to 800 g/10 min, and an intrinsic viscosity [η] of 0.01 to 10 dl/g, preferably 0.05 to 10 dl/g, more preferably 0.1 to 10 dl/g as determined at 135° C. in decahydronaphthalene.

The propylene polymer composition (A) preferably provides a DSC (differential scanning calorimeter) endothermic curve in which there is a maximum peak of melting point (Tm, ° C.) at 100° C. or above. The heat of fusion is preferably in the range of 5 to 40 J/g, more preferably in the range of 5 to 35 J/g. The maximum endothermic peak (melting point) of the propylene polymer composition (A) is 130° C. or above, preferably 140° C. or above, more preferably 160° C. or above.

The melt tension (MT) of the propylene polymer composition (A) is generally in the range of 0.5 to 10 g, preferably in the range of 1 to 10 g, leading to excellent forming properties into films and tubes. As used herein, the melt tension (MT) is a tension applied to a filament (strand) when the strand being extruded at 200° C. and an extrusion speed of 15 mm/min is withdrawn at a constant rate (10 m/min), and is measured with a melt tension tester (manufactured by Toyo Seiki Seisaku-Sho, Ltd.).

Desirably, the propylene polymer composition (A) can give formed products having cloudiness (haze) of not more than 25%, preferably not more than 20% as determined in accordance with ASTM D 1003.

(b1) When a tube being made of the composition (A) and having an inner diameter of 2.1 mm, an outer diameter of 3.5 mm and a length of 20 cm is looped by inserting both ends thereof into a hollow jig having a hole 10 mm in diameter and 5 mm in height and, then, the both ends of the tube are pulled down until a kink occurs in the loop, the distance H from the upper surface of the jig to the upper end of the loop is not more than 60 mm, preferably not more than 55 mm, more preferably not more than 50 mm.

Medical Tubes

The medical tubes according to the invention are fabricated from the aforementioned propylene polymer composition (A).

The medical tubes of the propylene polymer composition (A) may be manufactured using a common extruder under known extrusion conditions. For example, the propylene polymer composition (A) may be molten in a single screw extruder, a kneading extruder, a ram extruder or a gear extruder and be extruded through a circular die, followed by cooling.

The medical tubes may have a multi-layer structure as required, such as for preventing adsorption of chemicals to the inner surface or imparting heat resistance, without impairment of the medical tube performance.

The medical tubes of the propylene polymer composition according to the present invention are well balanced in properties such as transparency, kink resistance, flexibility, heat resistance, scratch resistance and rubber elasticity, and sufficiently satisfy the performance required as medical tubes.

The medical tubes of the invention have outer diameters in the range of 3.30 to 4.80 mm, preferably 3.30 to 4.75 mm, more preferably 3.30 to 4.70 mm, and inner diameters ranging from 1.95 to 3.21 mm, preferably 2.05 to 3.16 mm, more preferably 2.10 to 3.16 mm.

Preferably, the medical tubes satisfy the following (b2) and (b3):

(b2) The tubes have hardness in the radial direction (bounce generated when the tubes are collapsed in the radial direction) in the range of 0.10 to 0.50 kgf, preferably 0.15 to 0.45 kgf, more preferably 0.20 to 0.40 kgf.

(b3) The tubes contain a lubricant in an amount of 0.1 to 0.4 wt %, preferably 0.15 to 0.35 wt %, more preferably 0.2 to 0.3 wt %, and still more preferably the upper limit of the lubricant content is 0.25 wt % (based on the weight of the medical tube (100 wt %)).

Examples of the lubricants include but are not limited to fatty acid amide compounds such as erucic acid amide, and metallic soaps such as calcium stearate. The above amount of lubricant is preferable in that the tube tackiness is lowered while maintaining excellent properties of the tubes.

Preferably, the following relation is satisfied between the outer diameter of the medical tube and the modulus in tension (Young's modulus; YM (MPa)) of the polymer composition (A):

When the tube outer diameter is from 3.30 to 3.80, preferably 3.30 to 3.60 mm and the tube inner diameter is from 1.95 to 2.25 mm:

YM=5 to 15 MPa, preferably 8 to 15 MPa

When the tube outer diameter is from 4.30 to 4.80 mm, preferably from 4.30 to 4.70 mm and the tube inner diameter is from 2.95 to 3.21 mm:

YM=6 to 23 MPa, preferably 9 to 23 MPa.

EXAMPLES

The present invention will be hereinafter described in greater detail by Examples, but it should be construed that the invention is in no way limited to those Examples.

The conditions for testing properties are as follows.

(I) Evaluation of Polymer

[Melting Point (Tm) and Glass Transition Temperature (Tg)]

Tm and Tg were obtained from a DSC endothermic curve, and Tm was determined by reading the temperature at the maximum peak position. Specifically, a sample was loaded into an aluminum pan, and the temperature was raised to 200° C. at a rate of 100° C./min, maintained at 200° C. for 10 minutes, and lowered to −150° C. at a rate of 100° C./min. The temperature was then increased at a rate of 10° C./min to obtain an endothermic curve, from which Tm and Tg were determined.

[Intrinsic Viscosity [η]]

The intrinsic viscosity was measured at 135° C. in decalin.

[Mw/Mn]

Mw/Mn was measured by GPC (gel permeation chromatography) in an orthodichlorobenzene solvent at 140° C.

(II) Evaluation of Composition and Medical Tube

[Evaluation of Kink Resistance]

The composition according to the invention was extruded into test tubes 2.1 mm in inner diameter and 3.5 mm in outer diameter, with a margin of error of plus or minus 0.1 mm.

The evaluation employed a jig that was a hollow cylinder (1) having a hole 10 mm in diameter and 5 mm in height. A tube (2) having an inner diameter of 2.1 mm, an outer diameter of 3.5 mm and a length of 20 cm was looped by inserting both ends thereof into the jig, and the both ends of the tube were slowly pulled down until a kink occurred in the loop. The loop length (H) at the occurrence of kink was obtained as indicator of the kink resistance. The shorter the loop length, the higher the kink resistance. (See FIG. 1.)

Further, test tubes 3.2 mm in inner diameter and 4.5 mm in outer diameter were formed and their kink resistance were measured as before.

[Measurement of Dynamic Viscoelasticity]

A specimen was twisted (torsion mode) at 10 rad/s over an area 10 mm in width and 38 mm in length and was heated from −100 to 100° C. at a heating rate of 2° C./min; the loss tangent tan δ and storage modulus G' were measured at each temperature by means of Rheometrics RDS-II.

[Tensile Test]

1. Permanent Set

A dumbbell specimen having 50 mm length, 30 mm-apart benchmarks (L0), 5 mm width and 1 mm thickness was fixed between chucks 30 mm apart. The specimen was then 100% strained (to a distance of 60 mm between the chucks) at a stress rate of 30 mm/min, maintained for 10 minutes and released for 10 minutes. The distance between the bench marks (L) (mm) was measured, and the permanent set was determined from the formula:

Permanent set(%):=[(L−L0)/L0]×100

2. Modulus in Tension (Young's Modulus)

A JIS No. 3 dumbbell specimen was tested for modulus in tension with a span of 30 mm, at a stress rate of 30 mm/min and 23° C. in accordance with JIS K 6301.

[Heat Resistance] Penetration Temperature (° C.)

A test specimen 1 mm thick was heated at a rate of 5° C./min and a plane indenter 1.8 mm in diameter was pressed against the specimen at 2 kg/cm² in accordance with JIS K 7196. The penetration temperature (° C.) was determined from a TMA curve.

[Haze (%)]

A test specimen 1 mm thick was tested with digital turbidity meter NDH-20D manufactured by NIPPON DENSHOKU to determine the haze.

[Abrasion Resistance Test]

A test specimen 2 mm in thickness was tested with a "Gakushin" abrasion tester manufactured by Toyo Seiki Seisaku-Sho, Ltd., as follows. The tip of a 45R SUS abrasion indenter (470 g) was covered with a cotton duck (No. 10), and was caused to abrade the specimen at 23° C., reciprocating 100 times at a rate of 33 reciprocating motions per minute and with a stroke of 100 mm. The gloss change (Δ Gloss) between before and after the abrasion was determined by:

$$\Delta \text{ Gloss} = \frac{(\text{Gloss before abrasion} - \text{Gloss after abrasion})}{\text{Gloss before abrasion}} \times 100.$$

[Tube Hardness]

The tube was collapsed 1 mm in the radial direction at a rate of 50 mm/min and the bounce (kgf) was measured with a universal tester (Autograph) manufactured by Shimadzu Corporation. The tip jig used in the measurement had a plane circular shape 6 mm in diameter.

[EOG Sterilization]

Sterilization was performed with ethylene oxide gas at 68° C. for 2 hours.

[Vapor Sterilization]

Sterilization was performed by showering 121° C. hot water for 1 hour.

[Tackiness Test]

A tackiness test was performed using an infusion system including infusion bags, the medical tubes of the invention, and clamps. Specifically, the fluid in the infusion bag was allowed to flow through the medical tube, and the medical tube was pinched with the clamp to block the flow. After 24 hours from the blocking of the fluid flow, the clamp was removed from the medical tube to count the seconds until the fluid restarted to flow. The tackiness was evaluated based on the seconds required.

This test was performed for 100 tubes fabricated from the same composition. The tackiness was evaluated as 0 second when the fluid restarted to flow immediately (in 0 second) in all the 100 tubes. The tackiness was evaluated as 0-7 seconds when the fluid restarted to flow immediately (in 0 second) in most of the 100 tubes but in up to 7 seconds in some tubes.

Synthetic Example 1

Synthesis of Propylene Polymer Having Isotactic Structure (Hereinafter, Also Referred to as "Isotactic PP Elastomer")

A 2000-ml polymerizer sufficiently purged with nitrogen was charged with 833 ml of dry hexane, 100 g of 1-butene and 1.0 mmol of triisobutylaluminum at room temperature. The internal temperature of the polymerizer was raised to 40° C., and the pressure in the polymerizer (hereinafter, also referred to as the "system pressure") was increased to 0.76 MPa by feeding propylene. The system pressure was thereafter adjusted to 0.8 MPa by feeding ethylene. Subsequently, a toluene solution of 0.001 mmol of dimethylmethylene(3-tert-butyl-5-methylcyclopentadienyl) fluorenyl zirconium dichloride and 0.3 mmol in terms of aluminum of methylaluminoxane (manufactured by Tosoh Finechem Corporation) was added into the polymerizer. Polymerization was then carried out at an internal temperature of 40° C. for 20 minutes while maintaining the system pressure at 0.8 MPa by feeding ethylene, and was terminated by addition of 20 ml of methanol, followed by depressurization. The polymerization solution was poured into 2 L of methanol to precipitate the polymer, and the polymer was vacuum dried at 130° C. for 12 hours.

The resultant polymer weighed 36.4 g and had an intrinsic viscosity [η] of 1.81 dl/g, a glass transition temperature Tg of −29° C., an ethylene (unit) content of 18 mol %, a butene (unit) content of 8 mol %, and a GPC molecular weight distribution (Mw/Mn) of 2.1. With respect to the heat of fusion, DSC measurement did not provide any distinct fusion peak. $^{13}$C-NMR provided that the triad tacticity of head-to-tail coupled propylene unit sequences was 95.0% or above.

Example 1

Preparation of Propylene Polymer Composition

A propylene polymer composition (1) was obtained by kneading the following in a twin screw extruder at 200° C.:

15 parts by weight of a homopolypropylene having an isotactic structure (hereinafter, also referred to as the "isotactic h-PP (1)") which was Mitsui Polypropylene (manufactured by Mitsui Chemicals, Inc., B101; MFR=0.5, Tm=165° C.); and 85 parts by weight of the isotactic PP elastomer (propylene/ethylene/butene random copolymer) The results are shown in Table 1.

The propylene polymer composition (1) was extruded into a tube using a tube forming machine (manufactured by PLA GIKEN CO., LTD.) constituted of a single screw extruder 40 mm in diameter fitted with a tube die, under the following conditions:

Extruder temperature setting: C1/C2/C3/C4/H/D1/D2=190/200/200/200/200/200/200(° C.)

Extrusion speed: 10 m/min

Tube size: 3.2 mm in inner diameter and 4.5 mm in outer diameter

The results are shown in Table 1.

Examples 2 to 4

Tubes were formed in the same manner as in Example 1, except that the propylene polymer compositions were obtained as described in Synthetic Example 1 using the components in the amounts given in Table 1. The results are shown in Table 1.

Comparative Example 1

A tube was formed in the same manner as in Example 1, except that the propylene polymer composition was replaced with polybutadiene (R810 manufactured by JSR Corporation). The results are shown in Table 1.

Comparative Examples 2 and 3

Tubes were formed in the same manner as in Example 1, except that the propylene polymer composition was replaced with a resin composition that included syndiotactic homopolypropylene and syndiotactic polypropylene elastomer (propylene copolymer), obtained as described in WO 2004/067627. The results are shown in Table 1.

TABLE 1

|  | Ex. 1 | Ex. 2 | Ex. 3 | Ex. 4 | Comp. Ex. 1 | Comp. Ex. 2 | Comp. Ex. 3 |
|---|---|---|---|---|---|---|---|
| Isotactic h-PP(1) (wt %) MFR = 0.5 | 15 | 20 | 15 | 20 |  |  |  |
| Isotactic PP elastomer (wt %) C"3/C"2/C"4 = 74/18/8 (mol %) MFR = 8 | 85 | 80 | 85 | 80 |  |  |  |
| Syndiotactic h-PP (wt %) MFR = 10, Tm = 126° C. |  |  |  |  |  | 25 | 27 |
| Syndiotactic PP elastomer (wt %) C"3/C"2 = 82/18 (mol %) MFR = 1.5 |  |  |  |  |  | 75 | 73 |
| Polybutadiene |  |  |  |  | 100 |  |  |
| Outer diameter (mm) | 4.5 | 4.5 | 3.5 | 3.5 | 4.4 | 4.5 | 3.4 |
| Inner diameter (mm) | 3.2 | 3.1 | 2.2 | 2.1 | 3.1 | 3.2 | 2 |
| Young's modulus (MPa) | 9 | 12 | 9 | 12 | 20 | 3.5 | 4 |
| Heat resistance (° C.) | 125 | 135 | 125 | 135 | 70 | 100 | 100 |
| Kink resistance (mm) | 40 | 46 | 20 | 22 | 42 | 40 | 20 |
| Breaking strength (*1) (N) | 73 | 104 | 58 | 72 | 93 | 49 | 41 |
| Tube hardness (kgf) | 0.145 (1.42 N) | 0.215 (2.11 N) | 0.253 (2.48 N) | 0.371 (3.64 N) | 0.29 (2.8 N) | 0.23 (2.3 N) | 0.513 (5.03 N) |
| EOG sterilization (68° C.) | Not deformed | Not deformed | Not deformed | Not deformed | Not deformed | Not deformed | Not deformed |
| Vapor sterilization (121° C.) | Not deformed | Not deformed | Not deformed | Not deformed | Greatly deformed (unrecognizable as tube) | Deformed | Deformed |

(*1): Breaking strength of tube elongated in longitudinal direction

Synthetic Example 2

Synthesis of Propylene Polymer Having Isotactic Structure (Hereinafter, Also Referred to as "Isotactic PP Elastomer")

A 2000-ml polymerizer sufficiently purged with nitrogen was charged with 859 ml of dry hexane, 85 g of 1-butene and 1.0 mmol of triisobutylaluminum at room temperature. The internal temperature of the polymerizer was raised to 65° C., and the pressure in the polymerizer (hereinafter, also referred to the "system pressure") was increased to 0.76 MPa by feeding propylene. The system pressure was thereafter adjusted to 0.77 MPa by feeding ethylene. Subsequently, a toluene solution of 0.002 mmol of diphenylmethylene(3-tert-butyl-5-methylcyclopentadienyl)-2,7-di-tert-butylfluorenyl zirconium dichloride and 0.6 mmol in terms of aluminum of methylaluminoxane (manufactured by Tosoh Finechem Corporation) was added into the polymerizer. Polymerization was then carried out at an internal temperature of 65° C. for 30 minutes while maintaining the system pressure at 0.77 MPa by feeding ethylene, and was terminated by addition of 20 ml of methanol, followed by depressurization. The polymerization solution was poured into 2 L of methanol to precipitate the polymer, and the polymer was vacuum dried at 130° C. for 12 hours.

The resultant polymer weighed 67.6 g and had an intrinsic viscosity [η] of 1.42 dl/g, a glass transition temperature Tg of −24° C., an ethylene (unit) content of 14 mol %, a butene (unit) content of 19 mol %, and a GPC molecular weight distribution (Mw/Mn) of 2.1. With respect to the heat of fusion, DSC measurement did not provide any distinct fusion peak. $^{13}$C-NMR provided that the triad tacticity of head-to-tail coupled propylene unit sequences was 95.0% or above.

Example 5

Preparation of Propylene Polymer Composition

A propylene polymer composition (2) was obtained by kneading the following in a twin screw extruder at 200° C.:

15 parts by weight of a homopolypropylene having an isotactic structure (hereinafter, also referred to as the "isotactic h-PP (2)") which was Mitsui Polypropylene (manufactured by Mitsui Chemicals, Inc., B205; MFR=1.2, Tm 156° C.);

85 parts by weight of the isotactic PP elastomer (propylene/ethylene/butene random copolymer); and 0.22 parts by weight of an erucamide as a lubricant. The results are shown in Table 2.

The propylene polymer composition (2) was extruded into a tube using a tube forming machine (manufactured by PLA GIKEN CO., LTD.) constituted of a single screw extruder 40 mm in diameter fitted with a tube die, under the following conditions:

Extruder temperature setting: C1/C2/C3/C4/H/D1/D2=190/200/200/200/200/200/200(° C.)

Extrusion speed: 10 m/min

Tube size: 3.2 mm in inner diameter and 4.5 mm in outer diameter The results are shown in Table 2.

Further, a tube 2.1 mm in inner diameter and 3.5 mm in outer diameter was formed in the same manner as before, and the kink resistance was 23.

Examples 6 to 8

Tubes were formed in the same manner as in Example 5, except that the propylene polymer compositions were obtained as described in Synthetic Example 5 using the components in the amounts given in Table 2 and the inner and outer diameters were altered as in Table 2. The results are shown in Table 2.

Further, tubes 2.1 mm in inner diameter and 3.5 mm in outer diameter were formed in the same manner as before, and their kink resistance were 21 (Example 6), 22 (Example 7) and 21 (Example 8).

TABLE 2

|  | Ex. 5 | Ex. 6 | Ex. 7 | Ex. 8 |
|---|---|---|---|---|
| Isotactic h-PP(2) (wt %) MFR = 1.2 | 15 | 12 | 15 | 20 |
| Isotactic PP elastomer (wt %) C"3/C"2/C"4 = 74/14/8 (mol %) MFR = 8 | 85 | | | |
| Isotactic PP elastomer (wt %) C"3/C"2/C"4 = 67/14/19 (mol %) MFR = 8 | | 88 | 85 | 80 |
| Lubricant (ppm) | 2200 | 2200 | 2200 | 2200 |
| Outer diameter (mm) | 4.5 | 4.5 | 4.5 | 4.5 |
| Inner diameter (mm) | 3.1 | 3.2 | 3.2 | 3.2 |
| Young's modulus (MPa) | 12 | 5 | 8 | 12 |
| Heat resistance (° C.) | 135 | 125 | 125 | 125 |
| Kink resistance (mm) | 46 | 41 | 41 | 42 |
| Tackiness test (sec) | 0~7 | 0 | 0 | 0 |
| Breaking strength (*1) (N) | 104 | 85 | 91 | 99 |
| Tube hardness (kgf) | 0.215 (2.11 N) | 0.182 (1.78 N) | 0.21 (2.06 N) | 0.3 (2.94 N) |
| EOG sterilization (68° C.) | Not deformed | Not deformed | Not deformed | Not deformed |
| Vapor sterilization (121° C.) | Not deformed | Not deformed | Not deformed | Not deformed |

(*1): Breaking strength of tube elongated in longitudinal direction

The tackiness test of the tubes of Examples 6 to 8 showed that all the 100 tubes in each case allowed the fluid to reflow in 0 second after the blocking was released (tackiness: 0 second). The tackiness test of the tubes of Example 5 resulted in 97 tubes permitting the reflow in 0 second and 3 tubes permitting the reflow in 7 seconds after the blocking was released (tackiness: 0-7 seconds).

Accordingly, the tubes of Examples 6 to 8 were superior in non-tackiness to the tubes of Example 5.

INDUSTRIAL APPLICABILITY

The medical tubes of the present invention are well balanced in properties such as transparency, kink resistance, flexibility, heat resistance, scratch resistance and rubber elasticity, and sufficiently satisfy the performance required as medical tubes.

The invention claimed is:

1. A medical tube comprising a propylene polymer composition (A) that comprises a polymer with propylene units, at least part of the polymer having an isotactic structure and the total of the propylene units of the polymer being in an amount of 65 to 82 mol % (the total of the structural units of the polymer in the composition is 100 mol %), that comprises, based on 100 parts by weight thereof:
   (i) 1 to 40 parts by weight of isotactic polypropylene having an isotactic structure, in which the triad tacticity of the head-to-tail coupled propylene unit sequences as determined by $^{13}$C-NMR is at least 97.0%, and selected from the group consisting of a homopolypropylene and a propylene/α-olefin random copolymer containing α-olefin units in an amount of 0.3 to 5 mol % based on 100 mol % of the total of the structural units in the copolymer;
   (ii) 60 to 99 parts by weight of a propylene/ethylene/α-olefin random copolymer, in which the head-to-tail coupled propylene unit sequences have an isotactic structure, and the triad tacticity of the head-to-tail coupled propylene unit sequences as determined by $^{13}$C-NMR is at least 95.0%, and comprising 45 to 89 mol % of propylene units, 10 to 25 mol % of ethylene units and optionally 0 to 30 mol % of C4-20 α-olefin units, and that satisfies the following (a1), (a2) and (b1):
   (a1) the modulus in tension is in the range of 5 to 25 MPa as determined in accordance with JIS K 6301;
   (a2) the penetration temperature is 120° C. or above as determined in accordance with JIS K 7196; and
   (b1) when a tube being made of the composition (A) and having an inner diameter of 2.1 mm, an outer diameter of 3.5 mm and a length of 20 cm is looped by inserting both ends thereof into a hollow jig having a hole 10 mm in diameter and 5 mm in height and, then, the both ends of the tube are pulled down until a kink occurs in the loop, the distance H from the upper surface of the jig to the upper end of the loop is not more than 60 mm.

2. A medical tube according to claim 1, wherein the polypropylene (i) satisfies the following (i-a) and (i-b):
   (i-a) the melt flow rate (MFR; ASTM D1238, 230° C., 2.16 kg load) ranges from 0.01 to 400 g/10 min; and
   (i-b) the melting point as measured with a DSC is 120° C. or above.

3. A medical tube according to claim 1, wherein the intrinsic viscosity [η] at 135° C. in decalin of the propylene/ethylene/α-olefin random copolymer (ii) is desirably in the range of 0.01 to 10 dl/g.

4. A medical tube according to claim 1, wherein the propylene/ethylene/α-olefin random copolymer (ii) has a stress at 100% strain (M100) of not more than 4 Mpa when determined with respect to a JIS No. 3 dumbbell specimen, with a span of 30 mm at a stress rate of 30 mm/min and at 23° C. in accordance with JIS K 6301.

5. A medical tube according to claim 1, wherein the propylene/ethylene/α-olefin random copolymer (ii) satisfies the following (ii-a) and (ii-b):
   (ii-a) the crystallinity as measured by X-ray diffractometry is not more than 20;
   (ii-b) the glass transition temperature (Tg) as measured with a DSC is −10° C. or less.

6. A medical tube according to claim 1, wherein the propylene polymer composition (A) satisfies the following (A), (B), (C) and (D):
   (A) the loss tangent (tan δ) peak is at a temperature in the range of −25 to 25° C. according to dynamic viscoelasticity measurement (10 rad/s) in a torsion mode and the peak value is 0.5 or above;
   (B) the storage moduli G' (20° C.) and G' (100° C.) from the dynamic viscoelasticity measurement have a ratio (G' (20° C.)/G' (100° C.)) of not more than 5;
   (C) the penetration temperature (° C.) determined in accordance with JIS K 7196 is not less than 120° C.; and
   (D) the permanent set is not more than 20%, which is determined after the composition fixed between chucks 30 mm apart is 100% strained at a stress rate of 30 mm/min, maintained for 10 minutes and released for 10 minutes.

7. A medical tube according to claim 1, wherein
the bounce generated when the tubes are collapsed in the radial direction is in the range of 0.98 to 4.9 N; and a lubricant is contained in an amount of 0.1 to 0.4 wt % based on the weight of the medical tube (100 wt %).

8. A medical tube according to claim 1, wherein
the tube is fabricated from the propylene polymer composition (A) having the modulus in tension in the range of 5 to 15 and
the tube outer diameter is from 3.30 to 3.80 mm and the tube inner diameter is from 1.95 to 2.25 mm.

9. A medical tube according to claim 1, wherein
the tube is fabricated from the propylene polymer composition (A) having the modulus in tension in the range of 6 to 23 and
the tube outer diameter is from 4.30 to 4.80 mm and the tube inner diameter is from 2.95 to 3.21 mm.

* * * * *